United States Patent [19]

Sugimori et al.

[11] Patent Number: 4,576,733
[45] Date of Patent: Mar. 18, 1986

[54] 4-HALOGENOBENZOIC ACID ESTERS

[75] Inventors: Shigeru Sugimori, Fujisawashi; Toyoshiro Isoyama; Yasuyuki Goto, both of Yokohamashi, all of Japan

[73] Assignee: Chisso Corporation, Osaka, Japan

[21] Appl. No.: 755,720

[22] Filed: Jul. 17, 1985

[30] Foreign Application Priority Data

Jul. 19, 1984 [JP] Japan .................................. 59-150239

[51] Int. Cl.$^4$ ........................ G09K 3/34; C07C 121/60
[52] U.S. Cl. ............................ 252/299.67; 252/299.63; 558/416
[58] Field of Search ............... 260/465 D; 252/299.67

[56] References Cited
U.S. PATENT DOCUMENTS 4,198,312  4/1980  Sato et al. ........................... 252/299

Primary Examiner—Dolph H. Torrence
Attorney, Agent, or Firm—Wenderoth, Lind & Ponack

[57] ABSTRACT

A novel 4-halogenobenzoic acid derivative useful as a component constituting a liquid crystal composition having a large value of dielectric anisotropy and also a large value of optical anisotropy, and a liquid crystal composition containing the same are provided, which derivative is expressed by the formula

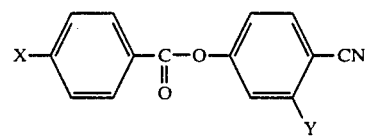

wherein X and Y, each represent F, Cl or Br.

4 Claims, No Drawings

4-HALOGENOBENZOIC ACID ESTERS

BACKGROUND OF THE INVENTION

This invention relates to novel liquid crystal compounds and liquid crystal compositions containing the same.

Display elements utilizing liquid crystals have been broadly used for watches, electric calculators, etc. These liquid crystal display elements utilize the optical anisotropy and dielectric anisotropy of liquid crystal substances, and the liquid crystal phases include nematic liquid crystal phase, smectic liquid crystal phase and cholesteric liquid crystal phase. However, among these, display elements utilizing nematic liquid crystals have been most broadly practically used. Namely, correspondingly to the electro-optical effect which has been applied to liquid crystal display, display elements are classified into TN (twisted nematic) type, DS (dynamic scattering) type, guest-host type, DAP type, etc., and there vary properties required for liquid crystal substances used for these respective display elements. As for such liquid crystal substances, those which exhibit liquid crystal phases within a temperature range as broad as possible in the natural world are preferable. However, it is the present status that there is no substance which alone satisfies the above conditions, but several kinds of liquid crystal substances are mixed with one another or with non-liquid crystal substances, for practical use. The above substances are required to be stable to moisture, heat, air, etc.

Recently liquid crystal display elements capable of being driven under low voltage have been particularly required, and in order to satisfy such a requirement, a liquid crystal composition having a large value of dielectric anisotropy (hereinafter abbreviated to $\Delta\epsilon$) is usually required.

In general, a liquid crystal composition having an optional $\Delta\epsilon$ value is obtained by adequately blending a compound of a positive $\Delta\epsilon$ value with that of a negative $\Delta\epsilon$ value. Thus in order to obtain a liquid crystal composition of a large $\Delta\epsilon$ value, a component having a large $\Delta\epsilon$ value as possible may be used, and in that case, such a component should be a compound which has a good compatibility with other components and broadens or at least does not narrow the mesomorphic range of the resulting composition.

On the other hand, by using a liquid crystal composition having a large value of optical anisotropy (hereinafter abbreviated to $\Delta n$), it is possible to inhibit occurrence of color unevenness due to partially uneven distance between substrates of liquid crystal cell and to reduce the distance between the substrates; the reduced cell distance results for the composition in an advantage of increase in the intensity of electric field even under the same impressed voltage. Thus a compound which increases a $\Delta n$ value of the resulting composition has been required.

SUMMARY OF THE INVENTION

The object of the present invention is to provide a novel compound useful as a component constituting a liquid crystal composition suitable to the above uses.

The present invention in a first aspect resides in a 4-halogenobenzoic acid ester expressed by the general formula

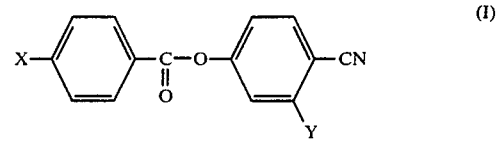

wherein X and Y each represent F, Cl or Br.

The present invention in a second aspect resides in a liquid crystal composition containing a 4-halogenobenzoic acid ester expressed by the above formula (I) wherein X and Y each represent F, Cl or Br.

DETAILED DESCRIPTION OF THE PREFERRED EMBODIMENTS

The compound of the present invention has a good compatibility with many other liquid crystal compounds such as esters, Schiff's bases, biphenyls, phenylcyclohexanes, heterocyclic compounds, etc., and when it is added in a small quantity to a liquid crystal composition, it is possible to increase the $\Delta n$ and also $\Delta\epsilon$ of the composition, and reduce the driving voltage of liquid crystal display elements using the composition.

The compound of the present invention may be prepared for example as follows:

3-Halogenophenol (II) and chloroform are first subjected to Reimer-Tiemann reaction in the presence of NaOH, followed by separating from the resulting halogeno-oxybenzaldehyde mixture, a 2-halogeno-4-hydroxybenzaldehyde (III), converting this (III) to an oxime (IV) with hydroxylamine, and then dehydrating this (IV) in acetic anhydride to obtain a 3-halogeno-4-cyanophenylacetate (V), which is then hydrolyzed with an alkali to obtain a 3-halogeno-4-cyanophenol (VI), which is then reacted with a 4-halogenobenzoyl chloride (VII) in the presence of pyridine to obtain the objective 4-halogenobenzoic acid 3'-halogeno-4'-cyanophenyl ester (I). The above preparation is illustrated as follows:

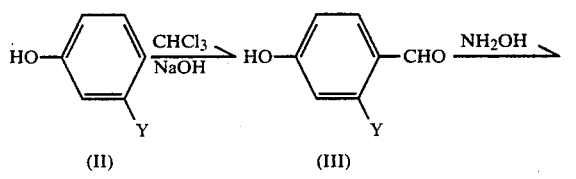

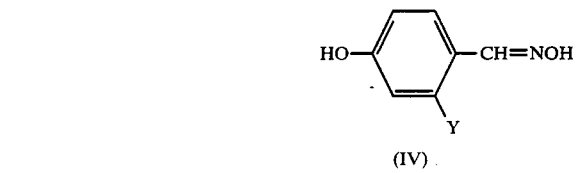

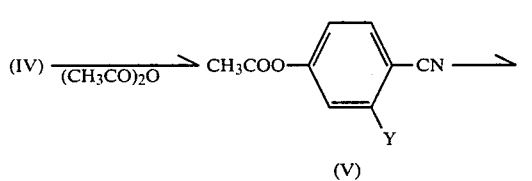

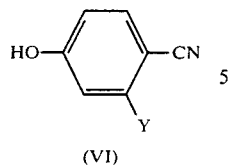

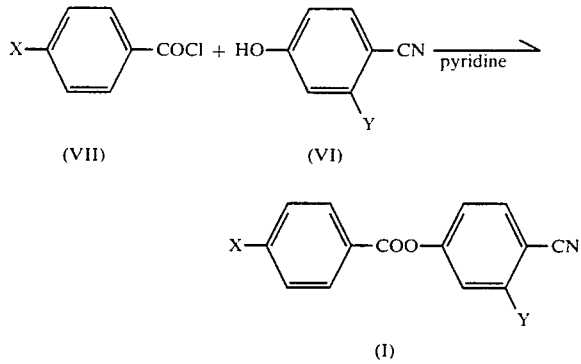

The composition of the present invention may be obtained by adding a small quantity of a 4-halogenobenzoic acid ester of the present invention to a mixture of compounds selected from esters, Schiff's bases, biphenyls, phenylcyclohexanes, heterocyclic compounds, etc. The quantity of the compound of the present invention added is 1 to 30% by weight, preferably 5 to 15% by weight.

Examples of ester liquid crystal compounds are trans-4-alkylcyclohexanecarboxylic acid 4'-alkylphenyl esters, trans-4-alkylcyclohexanecarboxylic acid 4'-alkoxyphenyl esters, 4-alkoxybenzoic acid 4'-alkylphenyl esters, 4-alkylbenzoic acid 4'-cyanophenyl esters, 4-(trans-4-alkylcyclohexyl)benzoic acid 4'-cyanophenyl esters, etc. Examples of Schiff's base liquid crystal compounds are 4-alkoxybenzylidene-4'-alkylanilines, 4-alkoxybenzylidene-4'-cyanoanilines, etc. Examples of biphenyl liquid crystal compounds are 4'-alkyl-4-cyanobiphenyls, 4'-alkoxy-4-cyanobiphenyls, 4'-alkoxy-4-alkylbiphenyls, etc. Examples of phenylcyclohexane liquid crystal compounds are trans-4-alkyl-(4-cyanophenyl)cyclohexanes, trans-4-alkyl-(4-alkoxyphenyl)cyclohexanes, etc. Examples of heterocyclic liquid crystal compounds are 5-alkyl-2-(4-cyanophenyl)-1,3-dioxanes, 5-alkyl-2-(4-cyanophenyl)pyrimidines, 5-cyano-2-(4-alkylphenyl)pyrimidines, etc.

The composition of the present invention consists, for example, of 70 to 99% by weight of a mixture of one to several kinds of trans-4-alkyl-(4-cyanophenyl)cyclohexanes and 1 to 30% by weight of 4-halogenobenzoic acid ester derivatives of the present invention, and it consists preferably of 85 to 95% by weight of the former and 5 to 15% by weight of the latter.

A concrete example of one to several kinds of trans-4-alkyl-(4-cyanophenyl)cyclohexanes in the above composition is 20 to 35 parts by weight of trans-4-propyl-(4-cyanophenyl)cyclohexane, 30 to 45 parts by weight of trans-4-pentyl-(4-cyanophenyl)cyclohexane and 20 to 35 parts by weight of trans-4-heptyl(4-cyanophenyl)cyclohexane. Examples of the alkyls of the trans-4-alkyl-(4-cyanophenyl)cyclohexanes are methyl, ethyl, butyl, hexyl, octyl, nonyl, decyl, etc. beside the above-mentioned alkyls.

The compound and the composition of the present invention will be described in more detail by way of Examples.

EXAMPLE 1

4-Fluorobenzoic acid 3'-fluoro-4'-cyanophenyl ester

4-Fluorobenzoyl chloride (2.1 g, 13 mmols) was added with stirring to a solution of 3-fluoro-4-cyanophenol (1.9 g, 14 mmols) dissolved in pyridine (5 ml). After completion of the reaction, the reaction mixture was allowed to stand overnight, followed by adding toluene (50 ml), pouring the resulting mixture into water, separating the toluene layer, washing the toluene layer with 6N hydrochloric acid, 2N NaOH solution and water in this order, finally drying over anhydrous sodium sulfate, distilling off toluene under reduced pressure, and recrystallizing the resulting colorless solids from ethanol to obtain the objective 4-fluorobenzoic acid 3'-fluoro-4'-cyanophenyl ester (2.3 g, 8.9 mmols, yield 68%) which had a melting point of 103.2°–104.2° C. A nematic-isotropic phase transition point (hereinafter abbreviated to N-I point) of this compound was found to be 12.1° C. according to extrapolation method where the compound was mixed with a liquid crystal composition of trans-4-alkyl-(4-cyanophenyl)cyclohexanes. Further, its elementary analysis values were as follows: C: 65.08% and H: 2.68% (calculated values: C, 64.87% and H, 2.72%).

EXAMPLE 2

Example 1 was repeated except that 4-fluorobenzoyl chloride of Example 1 was replaced by 4-chlorobenzoyl chloride to prepare 4-chlorobenzoic acid 3'-fluoro-4'-cyanophenyl ester. Its melting point was 117.8°–118.3° C. and its N-I point according to extrapolation method was 33.1° C. Its elementary analysis values: C, 61.31% and H, 2.60% (calculated values: C, 61.00% and H, 2.56%).

EXAMPLE 3 (APPLICATION EXAMPLE)

A liquid crystal composition (A) consisting of
trans-4-propyl-(4-cyanophenyl)cyclohexane, 30% by weight,
trans-4-pentyl-(4-cyanophenyl)cyclohexane, 40% by weight and
trans-4-heptyl-(4-cyanophenyl)cyclohexane, 30% by weight, had a N-I point of 52.1° C., a Δε of 11.2, a Δn of 0.119 and a viscosity at 20° C. of 23.4 cp. There was prepared a cell composed of two opposed substrates each having a transparent electrode of tin oxide coated with silicon oxide and subjected to rubbing treatment, and having a distance between the electrodes of 10 μm. The above liquid crystal composition (A) was sealed in this cell and the specific features of the resulting liquid crystal cell were measured. As a result, the threshold voltage (hereinafter abbreviated to Vth) was 1.54 V, and the saturation voltage (hereinafter abbreviated to Vsat) was 2.13 V.

A composition obtained by adding 4-fluorobenzoic acid 3'-fluoro-4'-cyanophenyl ester (5% by weight) prepared in Example 1 to the above liquid crystal composition (A) (95% by weight) had a N-I point of 50.1° C., a Δε of 12.6, a Δn of 0.121 and a viscosity at 20° C. of 25.4 cp. Further, when this composition was filled in the same cell as the above, the resulting liquid crystal cell had a Vth of 1.43 V and a Vsat of 2.00 V, that is, these values both lowered to a large extent.

EXAMPLE 4

A liquid crystal composition obtained by adding 4-chlorobenzoic acid 3'-fluoro-4'-cyanophenyl ester prepared in Example 2 (10% by weight) to the liquid crystal composition (A) used in Example 3 (90% by weight) had a N-I point of 50.2° C., a Δε of 12.0, a Δn of 0.120 and a viscosity at 20° C. of 29.5 cp. A liquid crystal cell using this composition had a Vth of 1.43 V and a Vsat of 1.98 V.

What we claim is:

1. A 4-halogenobenzoic acid ester expressed by the general formula

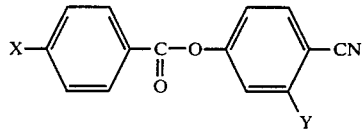

wherein X and Y each represent F, Cl or Br.

2. 4-Fluorobenzoic acid 3'-fluoro-4'-cyanophenyl ester according to claim 1.

3. 4-Chlorobenzoic acid 3'-fluoro-4'-cyanophenyl ester according to claim 1.

4. A liquid crystal composition having at least two components at least one of which is a compound set forth in claim 1.

* * * * *